United States Patent [19]

Alvarez et al.

[11] Patent Number: 5,443,989
[45] Date of Patent: Aug. 22, 1995

[54] METHOD FOR ASSESSING FETAL LUNG MATURITY USING AMNIOTIC FLUID SAMPLES

[75] Inventors: Juan G. Alvarez, Boston; Jack Ludmir, Chestnut Hill, both of Mass.

[73] Assignee: Beth Israel Hospital Association, Boston, Mass.

[21] Appl. No.: 140,569

[22] Filed: Oct. 25, 1993

[51] Int. Cl.6 ............................................. G01N 33/92
[52] U.S. Cl. ........................................ 436/71; 435/19; 435/7.1; 436/63; 436/162; 436/178
[58] Field of Search ................... 435/7.1, 19; 436/63, 436/71, 162, 178

[56] References Cited

U.S. PATENT DOCUMENTS

| | | | |
|---|---|---|---|
| 4,071,770 | 1/1978 | Shinitzky et al. | 250/461 B |
| 4,233,032 | 11/1980 | Statland et al. | 436/63 |
| 4,257,771 | 3/1981 | Yee | 436/71 |
| 5,156,950 | 10/1992 | Akino et al. | 435/7.51 |

OTHER PUBLICATIONS

Alvarez and Ludmir, *J. Chromatogr.* 615:142–147 (1993).
Touchstone & Alvarez, *J. Chromatogr.* 429:359–371 (1988).
Gluck et al., *Amer. J. Obstet. Gynec.* 109:440–445 (1971).
Gluck & Klovich, *Am. J. Obstet. Gynec.* 115:539–546 (1973).
Cherayil et al., *Obstet. Gynecol.* 50:682–688 (1977).
Thibeault & Hobel, *Am. J. Obstet. Gynecol.* 118:56–61 (1974).
Hallman et al., *Am. J. Obstet. Gynecol.* 125:613–617 (1976).
Garite et al., *Am. J. Obstet. Gynecol.* 147:681–686 (1983).
Towers & Garite, *Am. J. Obstet. Gynecol.* 160:298–303 (1989).
Torday et al., *New Eng. J. Med.* 301:1013–1018 (1979).
Steinfeld et al., *Obstet. Gynecol.* 79:460–464 (1992).
Farrel & Avery, *Am. Rev. Res. Dis.* 111:657–688 (1975).
Gluck et al., *Am. J. Obstet. Gynecol.* 120:142–155 (1974).
A. Lohninger et al, "Relationships among Human Amniotic Fluid Dipalmitoyl Lecithin, Postpartum Respiratory . . . " *Clin. Chem.* 29/4, 650–5 (1983).
S. Sax et al, "Liquid–Chromatographic Estimation of Saturated Phospho–lipid Palmitate in Amniotic Fluid . . . " *Clin. Chem.* 28/11, 2264–8 (1982).
J. Touchstone et al, "(3–sn–Phosphatidyl)cholines (Lecithins) in Amniotic Fluid", *Clin. Chem.* 29/11, 1951–4 (1983).
M. Tsai et al. "Improved Thin Layers Chromatography of Disaturated Phosphatidylcholine in Amniotic Fluid" *Clin. Chem.* 27/2, 239–42 (1981).

*Primary Examiner*—Carol A. Spiegel
*Attorney, Agent, or Firm*—Lahive & Cockfield

[57] ABSTRACT

The present invention provides an accurate, rapid and precise methodology for assessing maturity of the lungs in a fetus prior to birth, especially for premature fetuses having a gestation period of 37 weeks or less. The methodology quantitatively measures a specific phosphoglyceride, dipalmitoyl phosphatidyl choline, in samples of amniotic fluid for the assessment of fetal lung maturity. The process enzymatically cleaves such phophoglycerides and preferably detects the resulting diacylglycerols by HPTLC-reflectance spectrodensitometry.

7 Claims, 11 Drawing Sheets

METHOD FOR ASSESSING FETAL LUNG MATURITY USING AMNIOTIC FLUID SAMPLES

FIELD OF THE INVENTION

The present invention is concerned with the assessment of fetal lung maturity; and is particularly directed to a high-specificity assay for the determination of dipalmitoyl phosphatidyl choline in amniotic fluid samples as the means by which to assess if the fetal lung is mature, immature, or borderline in development.

BACKGROUND OF THE INVENTION

One of the major dilemmas that an obstetrician frequently encounters in his daily practice is whether or not to deliver a woman in preterm labor (onset of labor at $\leq 37$ weeks of gestational age), or to deliver or not a woman with some underlying disease that could be alleviated by terminating the preterm pregnancy. If the baby is delivered and the lungs of the baby are not mature or are borderline, the baby will develop Respiratory Distress Syndrome (or "RDS") which can result either in fetal death or long-lasting periods of repeated respiratory difficulty. The prevalence of RDS when the gestational age is below 31 weeks is 60%, but drops to 1% by a gestation of 36 weeks. It is estimated today that in the metropolitan Boston area alone the number of patients that need to be tested for the assessment of fetal lung maturity (or "FLM") is about 4,000 per year.

Immature fetal lungs lack an adequate surfactant layer which normally lines the alveoli and helps to keep the alveoli open after exhalation. The quantity of phospholipids generally in amniotic fluid, and of dipalmitoyl phosphatidyl choline (or "DPPC") in particular, has been correlated with the amount of surfactant lining the alveoli and with the degree of fetal lung maturity. Phosphatidyl choline (or "PC") fractional species represent nearly 80 percent of the surfactant phospholipid varieties in the fetal lung (Clements, *Am. Rev. Resp. Dis.* 101:984 (1970); and dipalmitoyl phosphatidyl choline (or "DPPC") constitutes about 60 percent of the fetal lung phosphatidyl choline species fraction. Other PC fraction species include 1-palmitoyl, 2-palmitoleoyl-PC (20%); 1-palmitoyl, 2-oleoyl-PC (10%); and other minor PC varietal species (10%). The remaining lung surfactant phospholipid components also include phosphatidyl inositol, phosphatidyl ethanolamine, sphingomyelin and phosphatidyl serine. Interestingly enough, the second major phospholipid of lung surfactants is phosphatidyl glycerol, comprising more than 10 percent of the mature surfactant in the lining of the lung (Pleger and Thomas, *Arch. Intern. Med,* 127:863 (1971); Hallman and Gluck, *Biochem. Biophys. Res. Commun.* 60:1 (1974).

A number of different assays and testing techniques have been developed and used as means for estimating fetal lung maturity-with markedly different degrees of success. Some of these conventionally known assay methods employ thin layer chromatography (or "TLC") as a requisite part of the assay. Nevertheless, despite the inclusion of TLC within these assays, and notwithstanding the improvements in the techniques of thin layer chromatography in the last decade, this chromatographic technique was viewed previously and remains seen today primarily as an ancestral technique and an undesirable mode of analysis for the medical field generally and the clinical environment in particular. This disinterest, reluctance and disfavor is intrinsically revealed within the range and diversity of publications reporting and describing these assays.

For instance, in 1971 a test for the assessment of FLM was introduced by Gluck and his associates [*Am. J. Obstet. Gynecol.* 109:440 (1971)]. This test measures the ratio of lecithin to sphingomyelin, phospolipids which are typically present in amniotic fluid and detected by thin layer chromatography (TLC). Subsequently, in 1976, Hallman et al. introduced the determination of phosphatidyl gylcerol (PG) in amniotic fluid by one-dimensional TLC as another test for the assessment of FLM [Hallman et al., *Am. J. Obstet. Gynecol.* 125:613(1976)]. A few years later, Kulovich et al. introduced the analysis of phosphatidyl glycerol (PG) in amniotic fluid using two-dimensional TLC [Kulovich et al., *Am. J. Obstet Gynecol.* 135:57 (1979)]. Surprisingly, since first introduced by Gluck and Hallman, TLC analysis of suffactant-associated phospholipids in amniotic fluid has become the "gold standard" for the assessment of fetal lung maturity. An L/S (Lecithin/Sphingomyelin) ratio value of $\geq 2$ or the detected presence of phosphatidyl glycerol (PG) in amniotic fluid are considered indicative of a mature fetal lung. Also, the term "lecithin" has become synonymous with and representative of a range of different phosphatidyl cholines (PC) generally; and today designates a variety of related species that differ from each other in their fatty add residue chain lengths and/or degree of unsaturation of the fatty acids sterified to the sn-1 and sn-2 position of the glycerol moiety commonly shared among them. Despite these developments, such TLC assay methods are viewed today as cumbersome at best.

Another overwhelming problem, however, remained in that none of these assays were suitable for the assessment of FLM in samples contaminated with blood, or with meconium, or for amniotic fluid samples obtained from the vaginal pool. In 1979 an alternative test was introduced by Torday et al. for the analysis of disaturated phosphatidyl choline species (or "DSPC") from amniotic fluid [*N. Engl. J. Med.* 301:1013 (1979)]. In this publication, the DSPC test was introduced as a method for the assessment of FLM in amniotic fluid samples contaminated with either blood or meconium. The cut-off value used in the Torday et al. assay of DSPC was 5 $\mu$g/mL; values above 5 $\mu$g/mL were considered mature fetal lung tissues. This DSPC test is based on the method originally described by Mason et al. for the isolation of disaturated phosphatidyl choline species using osmium tetroxide [*J. Lipid Res.* 17:281 (1976)]. A further adaptation of this method was also used to measure the concentration of DSPC species in rhesus-monkey amniotic fluid as a function of gestational age. It was found that the increase in amniotic fluid DSPC species correlated with lung maturity in the fetus.

A number of deficiencies and problems, however, exist in this DSPC assay method: The test measures total disaturated lecithins which includes a variety of different chemical entities in addition to DPPC; it uses low-resolution TLC; it requires relatively high volumes of amniotic fluid samples ($>1$ mL); it is a time-consuming test (4 to 5 h); and it acquires the use of highly toxic reagents (i.e., osmium tetraoxide and carbon tetrachloride). All of these flaws are substantive obstacles.

The historical reluctance and disfavor shown towards assays employing thin layer chromatography also lead to a continuing interest and desire, particularly by commercial pharmaceutical companies, for less complicated assay systems and less rigorous detection techniques for assessing fetal lung maturity. Thus by 1976, a new test for the assessment of FLM was introduced based on the analysis of membrane-bound vesicles in amniotic fluid by fluorescence polarization, as first described by Schinitzky et al. [*Br. J. Obstet. Gynaecol.* 83:833 (1976)]. In this method, a fluorophore is added to the amniotic fluid test solution containing the vesicles and the fluorophore is allowed to react with the vesicular membranes. Subsequently, when excited by plane polarized light of an appropriate wavelength, the fluorophore will emit its characteristic radiation with the same polarization as the incident light—if the molecule has not rotated with the vesicular membranes. In general, however, the angle of the emitted polarization light relative to that of the exciting light depends on how far the fluorescent molecule has interacted and rotated in the time between absorption and emission. Thus, the more fluid the vesicular membrane, the greater is the degree of rotation-resulting in relatively unpolarized fluorescent light in very fluid membranes and relatively more polarized light in less fluid membranes.

The early 1980's saw the general introduction of fluorescence polarization immunoassays for therapeutic drug monitoring determinations, with nearly every major medical center obtaining an optical instrument for this purpose such as the Abbott AMX-TDx Analyzer (Abbott Laboratories, Irving, Tex.). These instruments are highly automated and are now very well established in the clinical laboratory; and the fluorophore NBD-PC (N-[7-nitrobenz-2-oxa-1,3-diazol-4-yl]-phosphatidylchlorine) has been adapted for these instruments in a commercially available method [Tait et al., *Clin. Chem.* 3:2:248 (1986); Foerder et al., *Clin. Chem.* 32255 (1986)]. Although considerable controversy remains today as to the precise mechanism producing the observed results, this method yields results that correlate well with other measures of FLM; and, in a prospective study, compared favorably with the L/S ratio standards [Tait et al., *Clin. Chem.* 33:554 (1987)]. The method appears to have been quickly adopted by the medical and clinical community; and, since the test can be carried out with the AMX analyzer as a simplified, high volume, and low cost assessment of FLM, some obstetricians have been persuaded to use it as a more convenient test methodology than any of the TLC assays.

Another important test that is currently in use in hospitals across the country is the PG agglutination test which is based on the slide agglutination test of Garite et al. [*Am. J. Obstet. Gynecol.* 147:681 (1983)]. The results obtained in this study are typically compared to those data obtained by analysis of the L/S ratio, of phosphatidyl glycerol determination by TLC, and by fluorescence polarization for the assessment of FLM. The sensitivity of the PG agglutination test was judged to be near 100% and yielded a determined specificity of 65%. Test sensitivity is defined as the ability to predict FLM; test specificity is defined as the ability to predict the absence of FLM. In comparison, analysis by fluorescence polarization had a sensitivity of 100% and a specificity of 60% (40% falsely immature results).

More recently, in 1989,, Craig et al. introduced an ultrasensitive phosphatidyl glycerol (PG) detection kit based on the method described previously by Garite et al. [*Am. J. Obstet. Gynecol.* 160:298–303 (1989)]. This assay was said to have a lower limit of detection of 0.51 $\mu$g of PG/mL in amniotic fluid for a positive test; and the analysis could be performed within 20 to 30 minutes. Note that the original test kit described earlier by Garite et al. had a lower limit of detection of 2 $\mu$g/mL for a positive test. In their report, Craig et al. applied the ultrasensitive immunoreaction kit to the analysis of amniotic fluid obtained from the vaginal pool following premature rupture of membranes—i.e., samples contaminated with blood or meconium or patients with diabetes. Despite the lower threshold of PG detection necessary for a positive result in this new ultrasensitive test, the investigators concluded that the concordance rates were not significantly increased as compared to the results obtained by Garite et al. using the original kit. However, the data obtained using either of these kits have to be evaluated with caution in those situations where the samples are contaminated with meconium or obtained from the vaginal pool due to bacterial and/or human sperm contamination which have been shown to contain significant amounts of PG. Despite these flaws, this test is currently commercially available as the "Amniostat-FLM" test (Irvine Scientific, Calif.).

A number of other investigators have published a range of other assays methods and techniques for assessing fetal lung maturity. These have included the following systems: measurement of surfactant lecithin in sheep amniotic fluid [Ogawa, *J. Exp. Med.* 300:112 (1972)]; foam stability [Clements et al., *N. Eng. J. Med.* 286:1077 (1972)]; surface tension [Goldkrand, et al., *Am. J. Obstet. Gynecol.* 128:59 (1977)]; ratio of palmitic to stearic acid [Schirar et al., *Am. Obstet. Gynecol.* 121:653 (1975)]; surfactant apoprotein [King et al., *J. Appl. Physiol.* 39:735 (1975)]; and dipalmitoyl lecithin [Ogawa, *Biol. Neonate.* 28:18 (1976)]. With the possible exception of the amniotic fluid-foam-stability test, these methods have been difficult to use routinely or are not more reliable than the L/S ratio test or the analysis of PG by TLC, which thus remain as the gold standard for the assessment of FLM.

Overall, therefore, there remains today a continuing and long-standing need for a high-resolution, accurate and precise, and reliable assay by which to assess the maturity of fetal lung tissue. Moreover, recognizing the frequency with which amniotic fluid samples are contaminated with other living cells and body fluids, it is most desirable that such an assessment method not be markedly altered or meaningfully influenced by the presence of contaminants in the sample. Were such an assessment protocol developed, it would be recognized generally by persons in this field as a major advance and improvement over presently known tests.

SUMMARY OF THE INVENTION

The present invention provides a method for assessing the lung maturity of a fetus in a pregnant woman prior to labor, said method comprising the steps of:

providing a sample of the amniotic fluid surrounding the fetus in the pregnant woman, said amniotic fluid sample containing a representative aliquot of the lung surfactant phosphoglycerides then present within the lungs of the fetus;

combining said amniotic fluid sample with at least one enzyme in a reaction mixture for enzymatic cleavage of the polar head moiety of such lung surfactant phosphoglycerides as are present in said sample to release the corresponding diacylglycerols, wherein at least one of said enzymatically released diacylglycerols is diplamatoyl glycerol;

adding at least one organic solvent to said enzyme reaction mixture for organic solvent extraction and fluid organic phase separation of said released diacylglycerols from the remainder of said enzyme reaction mixture, said extracted diacylglycerols residing within a distinct organic solvent layer;

isolating and drying said organic solvent layer to yield a organic residue; and determining the quantity of dipalmitoyl glycerol in said organic residue using high resolution detection means, said determined quantity of dipalmitoyl glycerol serving as a measure of lung maturity in the premature fetus.

BRIEF DESCRIPTION OF THE FIGURES

The present invention may be more fully and easily understood when taken in conjunction with the accompanying drawing, in which.

DETAILED DESCRIPTION OF THE PRESENT INVENTION

Figure 1:
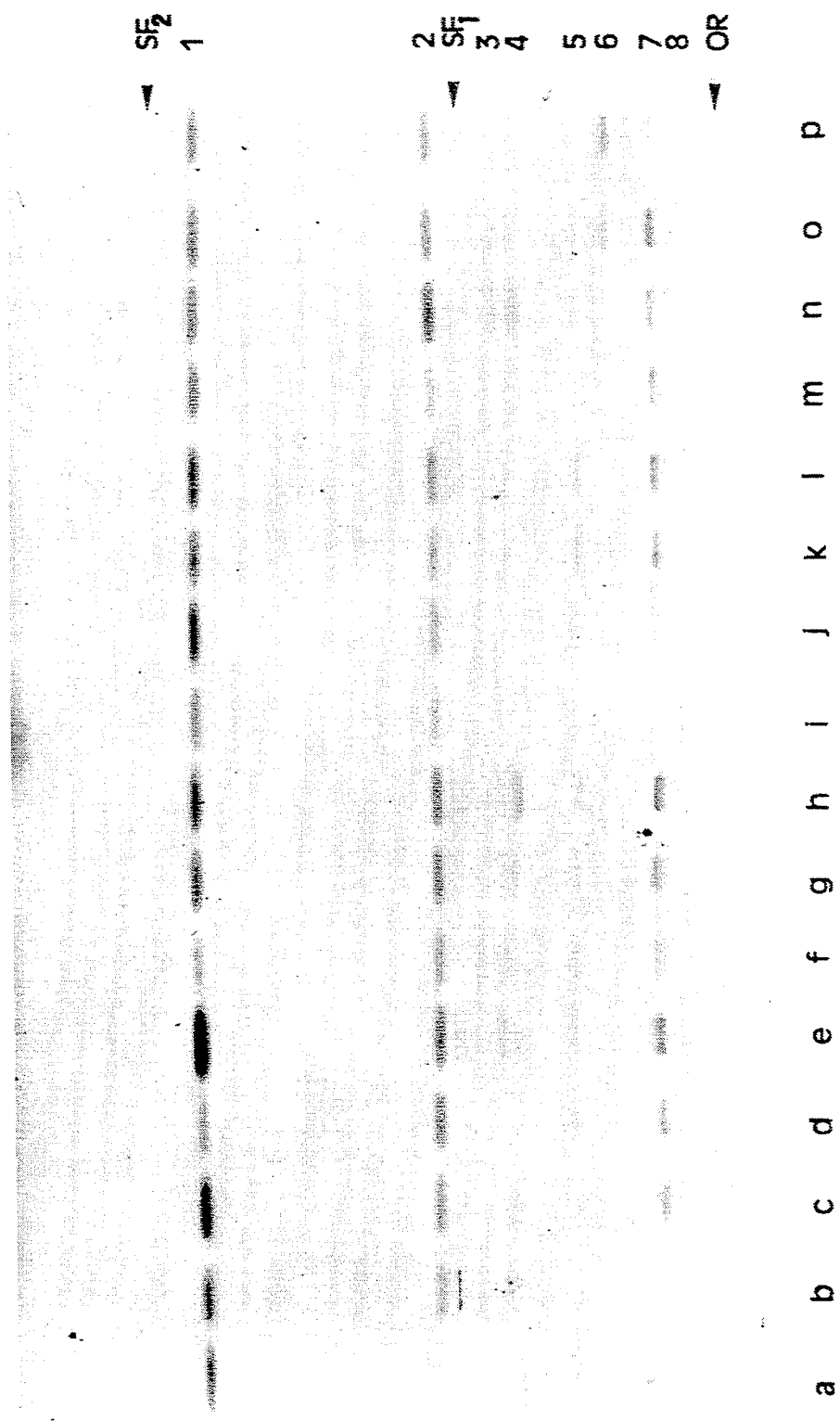
FIG. 1 is a photograph of CuSO$_4$-stained amniotic fluid lipids separated by one-dimensional high performance thin layer chromatography.

The present invention provides a preferred protocol and a general method for assessing the maturity status of lung tissue in a fetus prior to birth. The manipulations comprising the method provide a number of major benefits and unexpected advantages to the user. These include the following:

1. The methodology comprising the present invention is directed to monitoring the concentration in amniotic fluid of the major marker of fetal lung surfactant—phospholipid dipalmitoyl phosphatidyl choline or "DPPC" as a single, discrete species and chemical composition. The measurement of this lung surfactant-specific marker is achieved preferably using high resolution detection techniques that allow a close approximation at the surfactant lining of the alveoli.

2. The present assay methodology only requires 100 µL of amniotic fluid and it can be applied to the analysis of amniotic fluids contaminated with blood, meconium, creatinine, human spermatozoa, vaginal secretions, and vaginal mucosa cells as well as in pregnancies complicated with diabetes.

3. The test results provided by the present methodology are highly reproducible and can be made available within 30 minutes, typically at a rate of 8 samples/hour for the low patient volume/manual mode ( 1 sample/day), or alternatively at a rate of 50 samples/hour for a high patient volume/semiautomated mode (50 to 100 samples/day): The sensitivity of the test is near 100% and its specificity is at least 95%.

4. The present invention allows for using a variety of high resolution detection means for identification and quantitative measurement; and preferably employs high performance thin layer chromatography (or "HPTLC") as an integral part of the assay system. HPTLC has become one of the leading chromatographic techniques due to the recent introduction of automated instrumentation that has improved considerably the precision and detection limits of this particular mode of analysis. This instrumentation includes automated multisample applicators which allow application of up to 72 different samples per plate at variable volumes and application speed; horizontal development chambers that allow sample separation in both directions with minimal solvent requirements and development time; and scanning spectrodensitometers which permit scanning of the chromatograms in the reflectance and/or transmittance modes at a scanning speed of up to 20 mm s$^{-1}$. The combination of scanning spectrodensitometry and copper sulfate staining of the phospholipids separated by HPTLC, results in detection limits of the order of 20 ng/mL. The software capabilities of the spectrodensitometer computer permit transfer of the processed data to a modem or communications network system, thus, making the data directly available to a remote location bypassing a printed report. Using the aforementioned methodology, including sample preparation, a complete lipid profile report can be obtained in about 2 hours for up to 50 samples.

5. Unlike lecithin species from lung surfactant, lecithin fraction and other phospholipids from alternative sources including blood, meconium, vaginal secretions, vaginal epithelial cells and human spermatozoa contain only trace amounts of DPPC. A mathematical calculation shows that plasma and/or meconium would have to be concentrated forty-fold in order to be able to detect even trace amounts of DPPC (<1 µg/mL). Since the maximal concentration level of plasma and/or meconium contamination of an amniotic fluid sample is one-fold (100% blood an/or meconium), blood and/or meconium-contaminated samples of amniotic fluid can be safely used to measure lung surfactant-associated DPPC. Samples obtained from the vaginal pool can be contaminated with epithelial cells from the vaginal mucosa, vaginal secretions, bacteria, and human spermatozoa. It is estimated that the amniotic fluid sample would have to contain 10 billion spermatozoa in order to be able to detect even trace amounts of extraneous DPPC (<1 μg/mL). Therefore, DPPC is an ideal marker for the monitoring of lung surfactant-associated DPPC in amniotic fluid and therefore, for the assessment of FLM.

To aid in understanding and appreciating the merits of the present invention, the detailed disclosure will be made via a series of individual descriptive sections presented seriatim. Each individual section thus is merely one part of the totality of the disclosure and information described; and the reader is deemed to be fully informed as to how to make and use the methodology by the entirety of objective disclosure presented herein, section by section, cummulatively and collectively.

I. The Component Parts Of The Assessment Methodology And

The Chemical Basis Of Its Operation

The present methodology will assess the maturity status of fetal lung tissue from an amniotic fluid sample typically taken by a physician or nurse by amniocentesis or from the vaginal pool when the membranes are ruptured in the pregnant woman. The manner in which the amniotic fluid sample is obtained does not greatly limit or complicate the analysis; and although contaminants are preferably absent from the sample, the actual presence of blood, meconium, sperm, cells or other items from the vagina will not markedly affect or meaningfully influence either the accuracy or precision of the present methodology.

This assessment methodology employs and relies upon one specific chemical composition—dipalmitoyl phosphatidyl choline—as a marker and reactant. This specific phosphoglycerol as well as a diverse range of other phosphoglycerols and other phospholipids generally will be present intrinsically as part of the amniotic fluid sample taken from the pregnant woman. It is therefore useful to describe the nature and value of the different phospholipids, including those functioning as fetal lung surfactants, of amniotic fluid; and then to delineate how these classes of chemical compounds are manipulated in the assay.

A. The Different Chemical Classes Constituting Phospholipids

The amniotic fluid of the pregnant woman contains a variety of complex compounds which are loosely termed "phospholipids" or phosphatides—but are more precisely called "phosphoglycerides" or "glycerol phosphatides." It should be noted that not all phosphorus-containing lipids are phosphoglycerides—e.g., sphingomylein is a phosphiolipid because it contains phosphorus, but it is best classified as a sphingolipid because of the nature of the backbone structure to which the fatty acid residues are attached.

The general structure of phosphoglycerides as a class is shown by Table 1. The parent compound in each instance is the phosphoric ester of glycerol; and one or both of the other hydroxyl groups of glycerol are esterified with saturated or unsaturated fatty acids. In addition, all phosphoglycerides contain a polar head group or moiety, namely an alcohol designated generally as "X-OH" and whose hydroxyl group is esterified directly to the phosphoric acid moiety of the structure.

TABLE 1

General of Phosphoglycerides

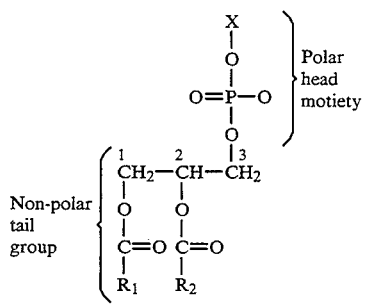

Wherein $R_1$ typically is a saturated fatty acid residue, and $R_2$ typically is an unsaturated fatty acid residue.

Since phosphoglycerides as a class of compounds each possess a polar head moiety in addition to their non-polar tail group, these compounds are amphipatic or polar phospholipids. The various types of phosphoglycerides constituting the class as a whole differ in the size, shape, and electric charge of their respective polar head moieties or groups. This is illustrated by the representative lung surfactant phosphoglycerides listed and described within Table 2 below. Each type of phosphoglyceride can exist as many different chemical species and structural forms—differing primarily in their fatty acid residue substitutes and in their non-polar tail groups. Typically, there is one saturated fatty acid residue (designated "$R_1$" herein) and one unsaturated fatty acid residue (designated "$R_2$" herein). For a more detailed description and an in-depth presentation of these phospholipids in general and phosphoglycerides in particular, the reader is directed to the text of Albert L. Lehninger, *Biochemistry*, 2nd Ed., Worth Publishers, Inc., 1975, pp. 287-295—the text of which is expressly incorporated by reference herein.

TABLE 2

Constituents of Lung Surfactant Phospholipids In Amniotic Fluid

| NAME | ABBREVIATION | PERCENTAGE OF TYPE IN AMNIOTIC FLUID | CHEMICAL STRUCTURE |
|---|---|---|---|
| Phosphatidyl Choline (or "Lecithin") | PC | ≈80%–85% | polar head moiety: $^+N(CH_3)_3$—$CH_2$—$CH_2$—$O$—$P(=O)(O^-)$—$O$— ; non-polar tail group: $CH_2$(1)—$CH$(2)—$CH_2$(3), with $O$—$C(=O)$—$R_1$ and $O$—$C(=O)$—$R_2$ |
| Dipalmitoyl Phosphatidyl Choline [or "Lecithin"] | DPPC | ≈45%–50% | polar head moiety: $^+N(CH_3)_3$—$CH_2$—$CH_2$—$O$—$P(=O)(O^-)$—$O$— ; non-polar tail group: $H_2C$(1)—$CH$(2)—$CH_2$(3), with $O$—$C(=O)$—$(CH_2)_{14}$—$CH_3$ on both positions |
| 1-Palmitoyl Phosphatidyl Choline | 1PPC | ≈85% | polar head moiety: $N(CH_3)_3$—$CH_2$—$CH_2$—$O$—$P(=O)(O^-)$—$O$— ; non-polar tail group: $H_2C$(1)—$CH$(2)—$CH_2$(3), with $O$—$C(=O)$—$(CH_2)_{14}$—$CH_3$ and $O$—$C(=O)$—$R_3$ |

TABLE 2-continued

Constituents of Lung Surfactant Phospholipids In Amniotic Fluid

| NAME | ABBREVIATION | PERCENTAGE OF TYPE IN AMNIOTIC FLUID | CHEMICAL STRUCTURE |
|---|---|---|---|
| 2-Palmitoyl Phosphatidyl Choline | 2PPC | ≈46% | polar head moiety: $^+N(CH_3)_3$—$CH_2$—$CH_2$—O—P(=O)(O)—O—; non-polar tail group: $H_2\overset{1}{C}$—$\overset{2}{CH}$—$\overset{3}{CH_2}$, position 1: C=O—$R_4$, position 2: O—C=O—$(CH_2)_{14}$—$CH_3$ |
| 1-Palmitoyl 2-Oleoyl Phosphatidyl Choline | POPC | ≈8% | polar head moiety: $^+N(CH_3)_3$—$CH_2$—$CH_2$—O—P(=O)(O)—O—; non-polar tail group: $H_2\overset{1}{C}$—$\overset{2}{CH}$—$\overset{3}{CH_2}$, position 1: O—C=O—$(CH_2)_{14}$—$CH_3$, position 3: O—C=O—$(CH_2)_7$—CH=CH—$(CH_2)_7$—$CH_3$ |
| Phosphatidyl Ethanolamine [or "cephaline"] | PEA | ≈3%–5% | polar head moiety: $^+NH_3$—$CH_2$—$CH_2$—O—P(=O)(O)—O—; non-polar tail group: $H_2\overset{1}{C}$—$\overset{2}{CH}$—$\overset{3}{CH_2}$, position 1: O—C=O—$R_1$, position 2: O—C=O—$R_2$ |

TABLE 2-continued

Constituents of Lung Surfactant Phospholipids In Amniotic Fluid

| NAME | ABBREVIATION | PERCENTAGE OF TYPE IN AMNIOTIC FLUID | CHEMICAL STRUCTURE |
|---|---|---|---|
| Phosphatidyl Inositol | PI | ≈2% | 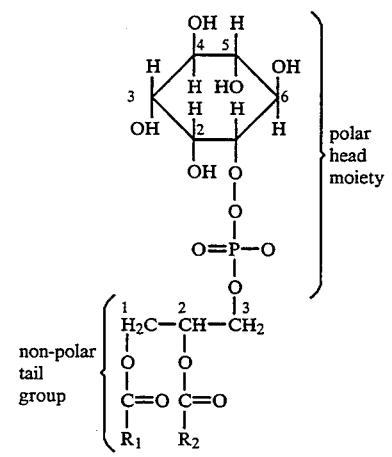 |
| Phosphatidyl Serine | PS | ≤1% | 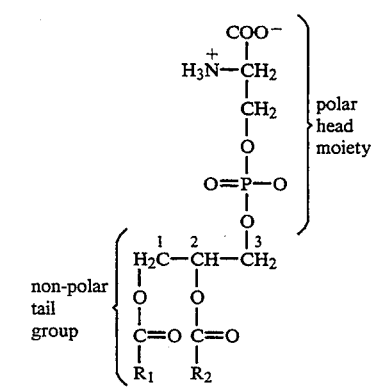 |
| Phosphatidyl Glycerol | PG | ≈6%–11% | 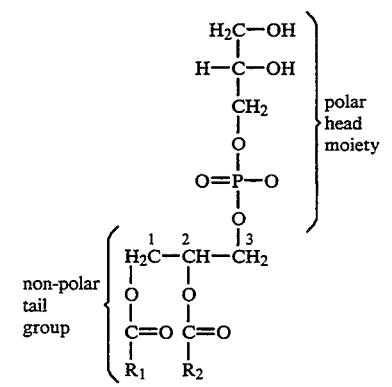 |

Wherein $R_1$ typically is a saturated fatty acid residue, and $R_2$ typically is an unsaturated fatty acid residue.
Wherein $R_3$ is not a palmitic acid residue.
Wherein $R_4$ is not a palmitic acid residue.

It will be noted and appreciated also that sphingolipids are a distinct chemical family of phospholipids which are markedly different from phosphoglycerides in structure and properties. The sphingolipid family includes the classes of sphingomyelins, neutral glycosphingolipids, and acidic glycosphingolipids (or gangliosides). Table 3 provides some illustrative examples of these entities.

It is seen that sphingomyelins in particular contain phosphorylcholine as their polar head moieties or groups; and are esterified to the 1-hydroxyl group or ceramide. Thus sphingomyelins have physical properties which are very similar to phosphatidyl choline (or lecithin); however, the chemical formulation and structure of sphingomyelins is meaningfully different from this phosphoglyceride.

TABLE 3

Sphingomyelins And Neutral Glycosphingolipids

| NAME | POLAR HEAD GROUP CONSTITUENT | ILLUSTRATIVE CHEMICAL STRUCTURE |
|---|---|---|
| Sphingomyelins | phosphorylcholine esterified to the 1-hydroxy group or ceramide | 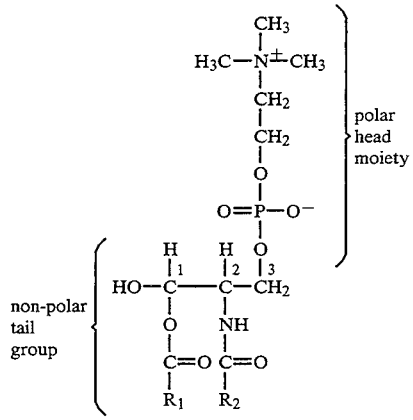 |
| | Wherein $R_1$ typically is a saturated fatty acid residue, and $R_2$ typically is an unsaturated fatty acid residue. | |
| Cerebrosides | a monosaccharide bound in β glycosidic linkage to the hydroxy group of ceramide | 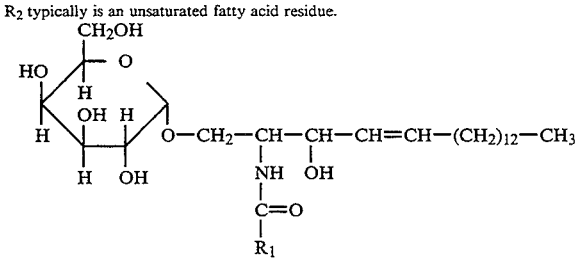 |
| | Where $R_1$ typically is a saturated fatty acid residue. | |

Where $R_1$ typically is a saturated fatty acid residue.

B. Enzymes Capable of Cleaving the Polar Head Moiety of Phosphoglycerides

At least one enzyme is to be combined with the amniotic fluid obtained from the pregnant woman to form a reactive mixture in order that specific cleavage of the polar head moieties of such phosphoglycerides occur; and that the non-polar tail groups of each cleaved phosphoglyceride be released as the corresponding diacylglycerol. The overall general enzyme reaction may thus be stated by Reaction I below as:

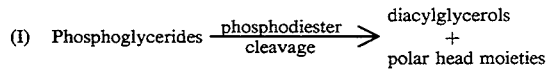

Of the different phosphoglycerides present in amniotic fluid, dipalmitoyl phosphatidyl choline is most representative quantitatively of the degree of maturity in fetal lung tissue. Accordingly, the specific enzyme reaction of interest may be stated by Reaction II below as:

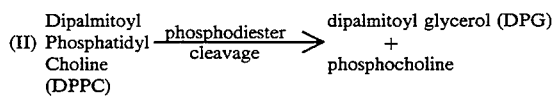

Among the enzymes capable and known to possess the enzyme specificity of cleaving the esterified phosphate bonds of lipids and releasing the many different polar head moieties from their respective antecedent phosphoglycerides are those listed within Table 4 below. While the specific conditions or environmental requirements for each of these may vary considerably, each nevertheless is able to perform the specific enzyme cleavages specified by Reactions I and II respectively.

TABLE 4

| Phospholipases* |
|---|
| phospholipase C |
| phospholipase D |
| phospholipase $A_1$ |
| phospholipase $A_2$ |

*Source: Dixon, M. and E. Webb, Enzymes, Academic Press, 1979.

Phospholipases (PL's) are enzymes that specifically hydrolye the ester bonds of phospholipids. Ester groups in general result from the reaction of an acid (R—COOH) with a base (R—OH) with loss of a molecule of $H_2O$. Phospholipase $A_1$ hydrolyzes the ester bond at the sn-1 position of glycerol-to yield free fatty acid and 1-OH-2-acylphosphorylcholine or also designated, 1-lysophosphatidylcholine. Phospholipase $A_2$ hydrolyzes the ester bond at the sn-2 position of the glycerol to yield 1-acyl-2-OH-phosphocholine or 2-lysophosphatidylcholine. Phospholipase C, on the other hand, hydrolyzes the phosphoester bond that links the primary hydroxyl group at the sn-3 position of glycerol to the phosphate group to yield phosphocholine and diacylglycerol. And finally, phospholipase D hydrolyzes the phosphoester bond that links the choline base to the phosphate group to yield choline and phosphatidic acid. This is illustrated by Reaction Scheme III below.

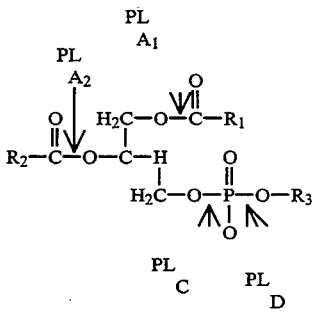

(III)

Wherein
R₁ is a fatty acid
R₂ is a fatty acid
R₃ is choline

Note also that treatment of the amniotic fluid sample with at least one enzyme such as phospholipase C is an obligatory step in order to release DPG from such DPPC as is present in the sample (as per Reaction Scheme II). No other or alternate steps are available that result in the specific hydrolysis of this phosphocholine moiety: i.e., acid hydrolysis is not suitable. Acid hydrolysis treatment would result in non-specific ester hydrolysis of all phospholipids generally. In contrast, phopholipases such as *Clostridum perfringes* phospholipase C are highly specific for phosphatidyl choline monolayers with almost negligible hydrolyric activity towards phosphatidyl ethanolamine, phosphatidyl serine phosphatidylinositol, and phosphatidyl glycerol Moreau et al., *Biochemistry* 27:2319 (1988)]; and thus, phospholipase C is most preferred for use by this methodology.

Matrix effects on the activity of *Clostridum perfringes* phospholipase C were tested empirically in a range of different mediums including blood, meconium, vaginal pool samples, and amniotic fluid samples with high concentrations of creatinine. Known amounts of DPPC (4 to 20 μg/mL) were added to the various matrixes and the rate of reaction monitored over a period of 1 h. No matrix effects were found on the rate of DPPC hydrolysis despite the diversity in chemical composition among the different mediums.

C. High Resolution Detection Means

A variety of different high resolution detection methods and materials may be used with the present invention. Most preferred is the technique of high performance thin layer chromatography (HPTLC). The desired format and processing is given below. Use of AgNO₃-Modified High-Performance Silica Layers in the stationary phase:

Resolution of the various diacylglycerols released following enzymatic hydrolysis of PC with phospholipase C requires the use of a high-resolution silica gel layers. The Whatman HP-K plate used in the development of this invention has an average particle size of 4.5 μm; and it therefore provides the higher number of theoretical plates which is required for high-resolution analyses. This is demonstrated by Equation 1 below.

$$Rs = N^{\frac{1}{2}}/4 \times (a-1)(k'/1+k') \quad \text{(EQ. 1)}$$

According to Equation 1 the resolution, "Rs" of a chromatographic system is directly proportional to the number of theoretical plates, "N" corresponding to the stationary phase utilized (HPLC column of HPTLC layer).

Other alternate commercial sources of high-resolution silica gel layers include Merck and Analtech, Inc. However, only Whatman Inc. presently provides the type of 5×5 cm plates that can be easily accommodated to small volumes of solvents and reagents used for development and visualization of the various lipids, respectively. The use of AgNO₃-modified high performance silica gel layers is an essential part of the invention. As shown below, interaction of the Ag⁺ ions in the silica gel

stationary phase with the π orbitals of the fatty acid double bond(s) during separation of the various lipids, allows the resolution of DPG from other diacylglycerols released from PC in which at least one of the fatty acids esterified to the glycerol moiety has one double bond. Another net effect of the use of AgNO₃-modified high performance layers combined to the use of low polarity index solvents—i.e., chloroform and acetone—is that those diacylglycerol species containing longer aliphatic chains migrated faster than those with shorter ones. This results in the migration of DPG faster than dimyristoylglycerol but slower than di-stearoylglycerol.

Chloroform-Acetone Solvent Mixtures In The Mobile Phase

The use of the chloroform-acetone solvent mixture (95:5.5, v/v) as the mobile phase for the separation of the various phospholipid diacylglycerols released (following enzymatic hydrolysis of amniotic fluid PC with phospholipase C) has been found to be an ideal solvent combination in that it provides resolution of the various diacylglycerol species and that it minimizes comigration of DPG with other non-polar lipid components including triglycerides and cholesterol separated under these conditions.

In adsorption chromatography, in addition to the modification of the silica gel stationary phase with reagents like AgNO₃ or boric acid, the only other major variable available to optimize the resolution of the solute molecules under analysis, is the chemical composition of the organic solvent mixture employed as the mobile phase. Fortunately, in adsorption chromatography, enormous variations in resolution and retention time [in the case of HPLC] or retardation factor [in the case of HPTLC] accompany variations in the solvent system; and only rarely can a suitable mobile phase not be found. The eluent strength ε°—which is the adsorption energy per unit area of solvent—can serve as a rough guide to the strengths of solvents for adsorption chromatography. This parameter depends upon the adsorbent with ε° values for silica gel being about 0.8.

For the selection a given solvent system for a particular separation in adsorption, two compatible solvents are chosen, one of which is strong (ε° is high) and the other which is weak (ε° is low). A suitable value for the capacity factor, k' is then obtained by varying the volume ratio of the two. In HPTLC, k' is calculated according to Equation 2 below where Rf is the retardation factor or ratio of the distance migrate by the solute versus the solvent front.

$$k' = (1 - Rf)/Rf \quad [\text{EQ. 2}]$$

It has been found that an increase in $\epsilon°$ value by 0.05 unit usually decreases all k' values by a factor of 3 or 4. Thus enormous variations in k' are possible; and at least one binary system involving the solvents in Table 5 can be found that will give adequate Rf values for nearly any sample. When overlapping peaks are encountered, exchanging one strong solvent for another while holding k' constant, will provide the desired solution.

TABLE 5

Eluent Strength of Common Chromatographic Mobile Phases

| Solvent | $\epsilon°$ |
| --- | --- |
| Hexane | 0.008 |
| Toluene | 0.230 |
| Diethyl ether | 0.300 |
| Chloroform | 0.320 |
| Acetone | 0.400 |
| Ethanol | 0.700 |
| Methanol | 0.760 |
| Water | 1.880 |

This standard approach to the separation of solutes by adsorption chromatography is thus applied to the resolution of the various diacylglycerols released following enzymatic hydrolysis of amniotic fluid phosphatidyl choline with phospholipase C. Since the silica gel is modified by the $AgNO_3$ reagent, the use of some of the solvents in Table 2 is precluded—i.e., methanol, water. However, since diacylglycerols are non-polar molecules containing long alkyl chains esterified at the sn-1 and sn-2 positions of the glycerol moiety, a solvent of a low polarity like chloroform, with high affinity for hydrophobic moieties, is preferably chosen. On the other hand, since some diacylglycerols have a free hydroxyl group at the sn-3 position (which confers some polarity to the molecule), ethyl acetate, acetone, dioxane and diethyl ether, may be added individually in combination with chloroform, to achieve separation of the various diacylglycerols-including dimyristoyl glycerol, dilauryl glycerol, dipalmitoyl glycerol, and 1-palmitoyl, 2-oleoyl-glycerol, all of which are the major diacylglycerol species typically found in amniotic fluid PC.

Note that the solvent combination chloroform-ethyl acetate (90:10, v/v) was initially tried for the separation of the various diacylglycerols. Chloroform has an $\epsilon°$ of 0.40 and ethyl acetate an $\epsilon°$ of 0.58. Since no separation of the diacylglycerol standard mixture was achieved using this solvent mixture as the mobile phase, the volume ratios were changed to 85:15, 90:10, and 95:5-also with no success. Therefore ethyl acetate was exchanged for another solvent of similar $\epsilon°$, such as acetone. Various volume ratios of chloroform-acetone were used as solvent mixtures. These included chloroform-acetone ratios of: 80:20; 85:15; 90:10; 91:9; 92:8; 93:7; 94:6; 95:5.5; 95:5; 96:4; 97:3; and 98:2. A volume ratio of chloroform-methanol 95:5.5 was found to give optimal resolution of the various diacylglycerols tested.

Alternative High Resolution Means for Detecting and Measuring DPG

Analysis of dipalmitoyl glycerol as a free diacylglycerol following enzymatic hydrolysis of amniotic fluid with phospholipase C may also be achieved by high-performance liquid chromatography (HPLC) and-/or gas chromatography (GC) using conventionally known techniques and commercially available equipment. The precise analytical details for the separation of the various diacylglycerols by either HPLC or GC are routine variables and factors open to personal choice by the user. Resolution of the various diacylglycerols using these methodologies is thus considered conventional in view of the prior art information and practices.

Another alternate methodology involves the measurement of dipalmitoyl glycerol using of an immunoreaction kit. Specific polyclonal antibodies against DPG may be obtained by procedures conventionally used every day within the field of immunology and immunochemistry. An immunoreaction kit is commercially available today for the measurement of phosphatidyl glycerol in amniotic fluid. The development of an immunoreaction kit for PG was greatly aided by the fact that this phospholipid contains a free hydroxyl group in the polar head that can be used as a nucleophile to conjugate PG to a hapten protein. Likewise, DPG has a free hydroxyl group at the sn-3 position of the glycerol which facilitates the conjugation of DPG to a hapten protein. The complex protein-DPG will act then as an immunogen when injected to recipient animals for the development of polyclonal antibodies. Following purification of the IgG fraction from the immunized animal that specifically reacts with the complex, these polyclonal antibodies specifically recognize DPG when present in biological fluids. A secondary antibody, coupled to a detection system (immuno peroxidase, fluorophore, radioactive isotope, latex particles) will then be used to specifically bind to the antigen-primary antibody complex and the concentration of DPG measured.

II. A Preferred Protocol For Performing The Assessment Methodology

The assay methodology can be rapidly and advantageously practiced and utilized by following the preferred protocol of manipulative steps as described below. It will be expressly recognized and understood that the procedures, techniques, timing, reagents, fluid concentrations, and aliquot volumes employed as stated herein are merely those most preferred for use; any or all of these may be changed as needed or desired. Moreover, the given specifics and particulars do not limit or restrict the range and variety of alternative compositions and/or manipulative choices which may be employed as substitutes, individually and collectively, at will or on-demand by the user when practicing the present methodology.

A. The Preferred Protocol:

Step 1

Thoroughly mix the amniotic fluid sample and transfer 100 μL of the sample to a glass conical tube.

Step 2

Add 200 μL of PBS or an isotonic buffer (pH 7.4) containing 4 mg/mL of phospholipase C (Sigma cat #P-7633) to the amniotic fluid sample. Add 200 μL of isotonic buffer alone to a separate 100 μL aliquot of amniotic fluid (control). Mix thoroughly.

Step 3

Incubate the mixture at 37° C. for 5 min. This reaction results in the specific cleavage of the polar head moiety of phosphatidyl choline and the subsequent release of the corresponding diacylglycerols. These diacylglycerols will differ from each other in their fatty acid chain length and/or degree of unsaturation.

Step 4

Add 1.8 mL of a mixture of chloroform-methanol (2:1, v/v), mix thoroughly, and centrifuge at 600 × g for 3 min to separate the emulsion in two isolated layers. This procedure results in the extraction of the lipids into the separated lower organic layer. It has been estimated using radiolabeled PC that addition of the chloroform-methanol mixture (2:1, v/v) to the enzyme reacted amniotic fluid sample in one cycle of organic solvent extraction results in a recovery efficiency of at least 95% of DPPC.

Step 5

Aspirate the separated lower organic (lipid containing) layer and transfer it as an isolated fluid to a glass conical tube.

Step 6

Evaporate the organic layer to dryness under a stream of nitrogen. This yields a dry organic residue.

Step 7

Dissolve the dry organic (lipid containing) residue in 101 μL of a solvent mixture containing chloroform-methanol (1:1, v/v). Mix thoroughly.

Step 8

Apply the resulting dissolved liquid in contiguous lanes as two 41 μL aliquots of sample and control to prewashed Whatman Hp-K silica gel plates [5×5 cm, 250 μm thickness, 4.5 μm average particle size] as 5 mm streaks, about 4 mm from the lower edge of the plate. Prior to sample application, the gel plates are immersed in a saturated solution of $AgNO_3$ in methanol for 1 min and dried thoroughly. If automated application is to be used, Whatman HP-K plates (10×10cm or 20×20 cm) and a Camag Linomat III Autosample are used for sample application. The samples will be individually applied at an interlane distance of 5 mm and a streak size of 5 mm.

Step 9

Apply 4 μL aliquots of the internal standard, DPG (0.1 mg/mL), to a different lane on the silica gel plates.

Step 10

Predevelop the plates in chloroform-methanol (1:1, v/v) to approximately 1 cm from the lower edge of the plate. This predevelopment results in the regrouping of the solute molecules as a thin band at the starting front therefore preventing Eddy diffusion-induced band broadening.

Step 11

Dry the plates thoroughly under a stream of warm air.

Step 12

Develop the plates by immersion in 10×10 cm glass tanks (Camag Scientific) to a distance of 4.5 cm using a chloroform-acetone mixture (95:5.5, v/v) as the mobile phase.

Step 13

Dry thoroughly under a stream of warm air.

Step 14

Dip the plates in a 10% solution of $CuSo_4$ $l$ $in$ 8% $H_3PO_4$ for 5 seconds, and allow the excess reagent to drip from the plates.

Step 15

Place the plates in an oven with initial and final temperatures of 24° C. and 125° C., respectively.

Step 16

Scan the $CuSO_4$-stained plates with a Shimadzu CS-9000 spectrodensitometer (or similar instrument) at 400 nm in the reflectance mode.

Step 17

Obtain the mean integration area for both sample (Xs) and control (Xc); subtract the mean control value from the sample value; divide by the integration area corresponding to the DPG internal standard (S) (0.4 μg); and multiply by 8—i.e., $$(Xs-Xc)/S \times 8 = DPPC]in\ \mu g/mL$$

This will give the actual concentration of DPG and, therefore, the concentration of DPPC in amniotic fluid in μg/mL.

B. Ease of Performance and Reproducibility of Test Results

As indicated in the detailed description of the preferred test protocol, two 4 μL aliquots were routinely applied to the HP-K plates and the average values obtained. Based on these results the intra- and interassay variation for the DPG test as measured by the standard deviation was 0.5% and 1%, respectively. Physicians participating in the residency program at the department of Ob&Gyn at Beth Israel Hospital in Boston, were asked to perform the test according to the described preferred protocol. After a step-by-step demonstration of the procedure, the various residents involved were asked to perform the test on two separate occasions under close supervision. The DPG test values obtained after the 3rd test performed by the resident was compared to those obtained by the inventors. No significant differences were found in the intra- and inter-assay variation values obtained by the various residents involved and those obtained by the inventors.

III. Substantive Differences Which Separate And Distinguish

The Present Methodology From Prior Art Assays

A. The Torday et al. analysis of disaturated phosphatidyl choline (the DSPC test) differs from the present methodology (the DPPC test) in that the DSPC test relies on the destruction of unsaturated PC by the osmium tetraoxide/carbon tetrachloride reagent, leaving a mixture of different disaturated lecithins (only one of which is DPPC) to be quantitated by densitometry. In the DSPC method no attempt is made to resolve DPPC from the various saturated PC species. In addition, some of the other major drawbacks of the DSPC test are that: it requires at least 1 mL of amniotic fluid for the analysis; it uses highly toxic reagents, and it is time-consuming taking at least 2 hours for the completion of the test.

B. In addition, Torday et al. reported a sensitivity of 99.5% and a specificity of 83% for the DSPG test as compared to 95 and 56% for the L/8 ratio and 94 and 60% for the PG test. Torday et al. also reported that centrifugation of the amniotic fluid sample resulted in a net loss of about 47% of the total DSPC present in the sample. Since DPPC is the major disaturated species in lung surfactant associated lecithins, the discrepancy in the DS PG and DPPG cut-off values (5 and 10 µg/mL, respectively) can be explained on the basis that centrifugation results in a net loss of almost 50% of DSPC. Taken all of these results together it becomes apparent that the DPG test described herein as the present invention is far superior to any of the existing methodologies currently in use for the assessment of FLM-in that it uniquely couples the use of the highly specific phophoglyceride lung surfactant marker DPPG to high resolution chromatography of DPG.

C. Although the Abbott-TDx test correlates well with the conventional L/S ratio assay, the precise mechanism by which this Abbott-TDx test measures FLM is not clear. Its adoption responds more to its simplicity, fast turn around time and to the fact that AMX instrumentation is currently available in almost every clinical laboratory than to its own merits as a specific test for the assessment of FLM. However, the fact that the Abbott-TDx test correlates so closely with the L/S ratio also results in inherently high rates of falsely immature results. The low specificity of the Abbott-TDx test (55%) coupled to the fact that it cannot be utilized in the evaluation of amniotic fluid samples contaminated with blood, creatinine or meconium; or in pregnancies complicated with diabetes, results in a high number of cases where FLM cannot be appropriately established.

D. The Amniostat-FLM test also inherits the low specificity values ascribed to the monitoring of PG in amniotic fluid as a minor component-single marker test. As indicated by Hallman et al., absence of PG in amniotic fluid does not mean that the RDS is inevitable.

IV. Experimental Studies And Empirical Data

To demonstrate the operation, merits, advantages, and value of the present methodology, several experimental studies were conducted and a variety of empirical evidence obtained, which are presented below. The described experiments and resulting data presented are demonstrative of the subject matter as a whole which is the present invention; and provide illustrative examples which indicate the range and variety of applications envisioned for the methodology. It will be noted and appreciated, also, that while the described experiments and empirical data are specific in their particulars, it will be expressly understood that those experiments and/or empirical data do not either limit or restrict the methodology in any way. To the contrary, those empirical results and experiments are merely representative of the many uses and applications in which the methodology can be advantageously employed.

Experimental Series I: The Capabilities of HPTLC Analyses

It is desirable initially to demonstrate and prove the capabilities of high-performance thin-layer chromatography (HPTLC) as a technique and mode of analysis suitable for the separation and identification of different phospholipids found in amniotic fluid (AF). Despite the significant growth that thin layer chromatography (TLC) has experimented in the last ten years, this chromatographic technique still remains regarded as an ancestral method of analysis in the clinical environment. HPTLC has become one of the leading chromatographic techniques due to the recent introduction of automated instrumentation that has improved considerably the precision and detection limits of this particular mode of analysis.

This instrumentation includes automated multi-sample applicators which allow application of up to 72 different samples per plate at variable volumes and application speed, horizontal development chambers that allow sample separation in both directions with minimal solvent requirements and development time, and scanning spectrodensitometers which permit scanning of the chromatograms in the reflectance and/or transmittance modes at a scanning speed of up to 20 mm $s^{-1}$. The combination of scanning spectrodensitometry and copper sulfate staining of the phospholipid and cholesteryl ester fractions separated by HPTLC results in detection limits of the order of 20 ng/ml [Touchstone et al., *Clin. Chem.* 29:1952 (1983)]. The software capabilities of the spectrodensitometer computer permit transfer of the processed data to a modem or communications network system, thus making the data directly available to a remote location bypassing a printed report. Using the aforementioned methodology, including sample preparation, a complete lipid profile report can be obtained in about 2 h for up to 50 samples.

In this experimental-series, analysis of the aforementioned lipids by semiautomated HPTLC is presented. Resolution of the various AF lipids, including cholesteryl palmitate, triglyceride fraction, cholesterol, free fatty acid fraction, phosphatidylglycerol, pseudophosphatidylglycerol, phosphatidylethanolamine, phosphatidylinositol, phosphatidylserine, phosphatidylcholine, sphingomyelin, and lysophosphatidylcholine, is accomplished in one dimension allowing, therefore, concurrent multisample analysis.

Chemicals and Reagents

The lipid standards, including cholesteryl palmitate, trioleoin, oleic acid, cardiolipin, phosphatidylglycerol, phosphatidylethanolamine, phosphatidylinositol, phosphatidylserine, phosaphatidylcholine, sphingomyelin, and lysophosphatidylcholine, were purchased from Sigma (St. Louis, Mo., USA). Precoated silica gel HP-K high-performance plates (10 cm × 10 cm, 250/µm thickness) were obtained from Whatman (Clifton, N.J., USA). Solvents were EM Science chromatographic grade. Inorganic salts were from J. T. Baker (Phillipsburg, N.J., USA) and of the highest purity available.

Sample Preparation

AF samples were obtained by transabdominal amniocentesis from women with gestational ages ranging between 28 and 38 weeks. Pregnancies complicated by diabetes mellitus or Rh sensitization were excluded. None of the patients had clinical signs or symptoms of chorioamnionitis and all fluid samples had negative cultures. Aliquots of 0.1 ml of the AF samples were added to glass conical tubes having screw-cap tops lined with PTFE, polytetrafluoroethylene) and extracted by liquid-liquid partition by addition of 0.6 ml of a mixture of chloroform-methanol (C-M) (2:1, v/v) to obtain a final ratio of C-M-AF of 4:2:1 (v/v). The tubes were then centrifuged at 800 g for 5 min, the water-saturated C-M lower phases aspirated separately and evaporated to dryness. The resulting lipid residues were redissolved in 10 μl of C-M (1:1, v/v).

High-Performance Thin-layer Chromatography

Aliquots of 4 μl were applied to the plates as 4-mm bands, 5 mm from the lower edge of the plate and at a speed of 800 nl/s using a Camag Automatic TLC Sampler III (Camag Scientific, Wilmington, N.C., USA). Following sample application, the plates were predeveloped in C-M (1:1, v/v) to ca. 1 cm from the lower edge of the plate, thoroughly dried, and developed in 25 cm × 25 cm size tanks using chloroform-ethanol-triethylamine-water (C-E-T-W) (30:34:30:8, v/v) for the first development (SF 1 ). This mobile phase allows separation of polar lipids, including sphingomyelin, phosphatidylcholine, lysophosphatidylchoine, phosphatidylserine, and phosphatidylinositol. Cardiolipin and phosphatidylglycerol comigrate as a single band following this first development. The plates were then dried at 24° C. in a vacuum oven for 5 min and placed in hexane-diethyl ether (H-E) (50:5, v/v) for the second development (SF$_2$). This mobile phase allowed separation of the cholesteryl ester fraction and resolution of phosphatidylglycerol, and cardiolipid. The plates were dipped for 5 s in a 10% solution of $CuSO_4$ in 8% $H_3PO_3$ [3], excess $CuSO_4$ allowed to drip off the plate, placed horizontally in an oven with initial and final temperatures of 24 and 120° C., respectively, and scanned with a Shimadzu CS-9000U spectrodensitometer at 310 nm in the reflectance mode using a beam size of 1 mm/5 mm.

In a different set of experiments, 100 ml of pooled term AF samples were extracted with six volumes of C-M (2: 1, v/v), the organic phase was evaporated to dryness, and the resulting residue redissolved in 1 ml of C-M (1:1, v/v). Aliquots of 200 μl were applied with the Camag Automatic TLC Sampler III as a 18-cm streak to Shatman HP-K silica gel plates, 10 cm × 20 cm, the plates predeveloped in C-M (1:1, v/v) and developed using C-E-T-W and H-E, as indicated above. The bands corresponding to cholesteryl palmitate, phosphatidylglycerol, phosphatidylinositol, phosphatidylcholine, and sphingomyelin were scrapped from the plate, and the lipids desorbed from the silica gel by addition of C-M-W (1:1:0.1, v/v) followed by centrifugation at 800 g for 5 min. The various C-M-W supernatants containing the individual lipids were evaporated to dryness and redissolved in 500 μl of C-M (1:1, v/v) to obtain a final concentration of 1 mg/ml. The purified lipids were then used to generate individual standard curve as follows: aliquots of the lipids isolated from AF dissolved in C-M were evaporated to dryness, and 0.5-ml aliquots of AF of low lipid content, as determined by HPTLC-reflectance spectrodensitometry (28–30 weeks of gestation), added to obtain concentrations that ranged from 0.04 to 4 μg/ml. The spiked samples were sonicated in a Branson 1200 ultrasonic bath (Danbury, Conn., USA) for three 30-s periods at 10-s intervals and brought to 1 ml with 0.5 ml of the same AF. Aliquots of 0.1 ml were then extracted and analyzed as indicated above. Quantitation was obtained by interpolation of the integration areas of the lipids under analysis with the standard curves generated for the individual lipids purified from AF.

Results

Figure 2:
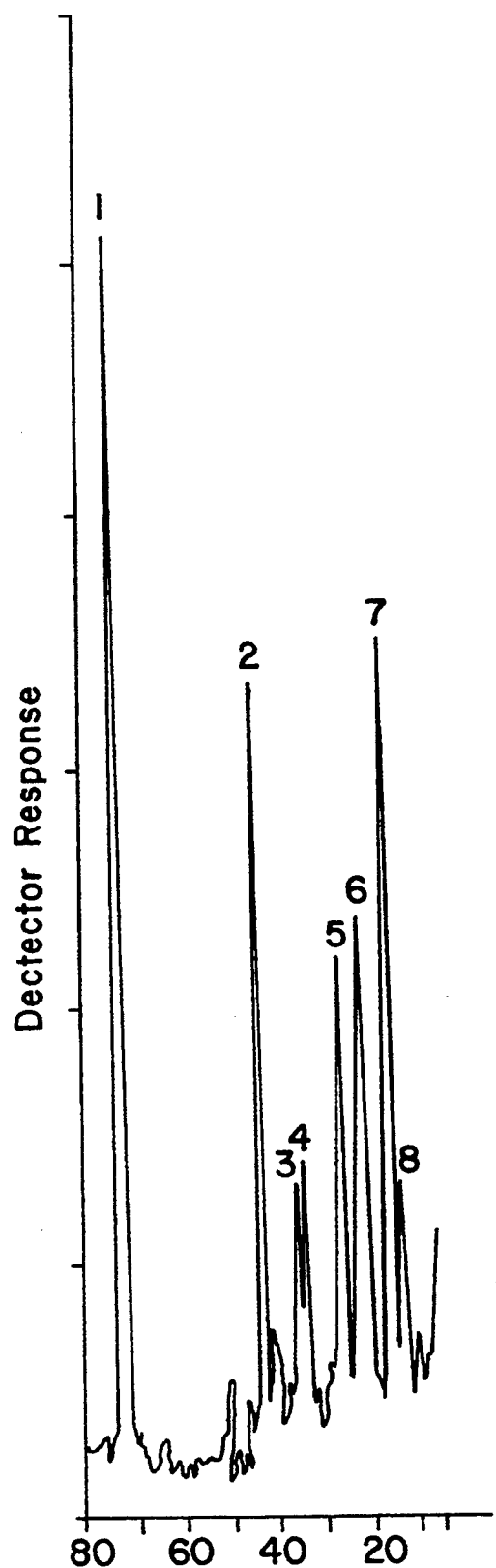
FIG. 2 is an illustration of an integrated high pressure thin layer chromatogram showing the separation of different and separately identifiable amniotic fluid lipids.
Figure 3A:
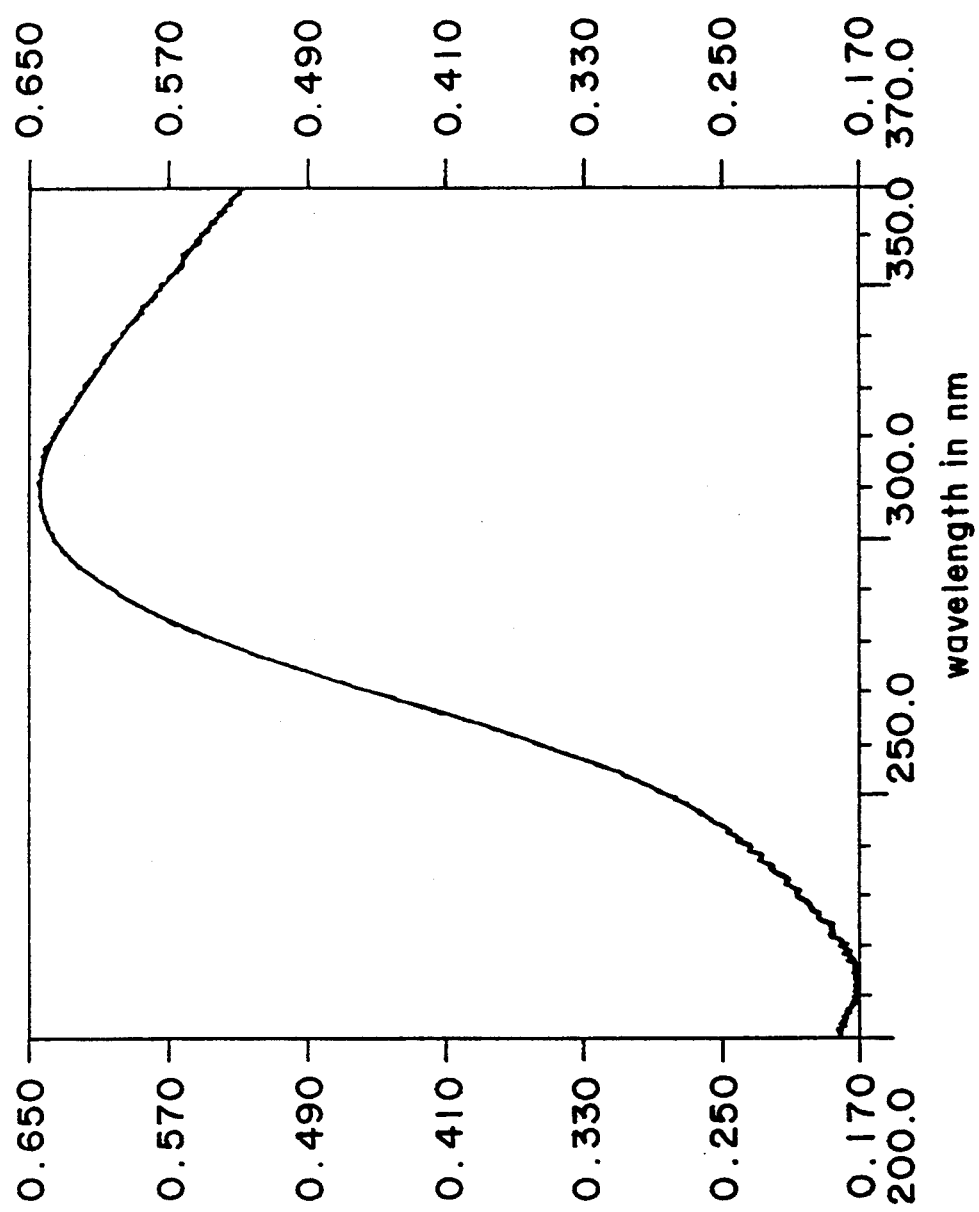
FIGS. 3A and 3B are graphs illustrating the ultraviolet and visible spectra of the CuSo$_4$-lipid chromagen obtained by high performance thin layer chromatography.
Figure 3B:
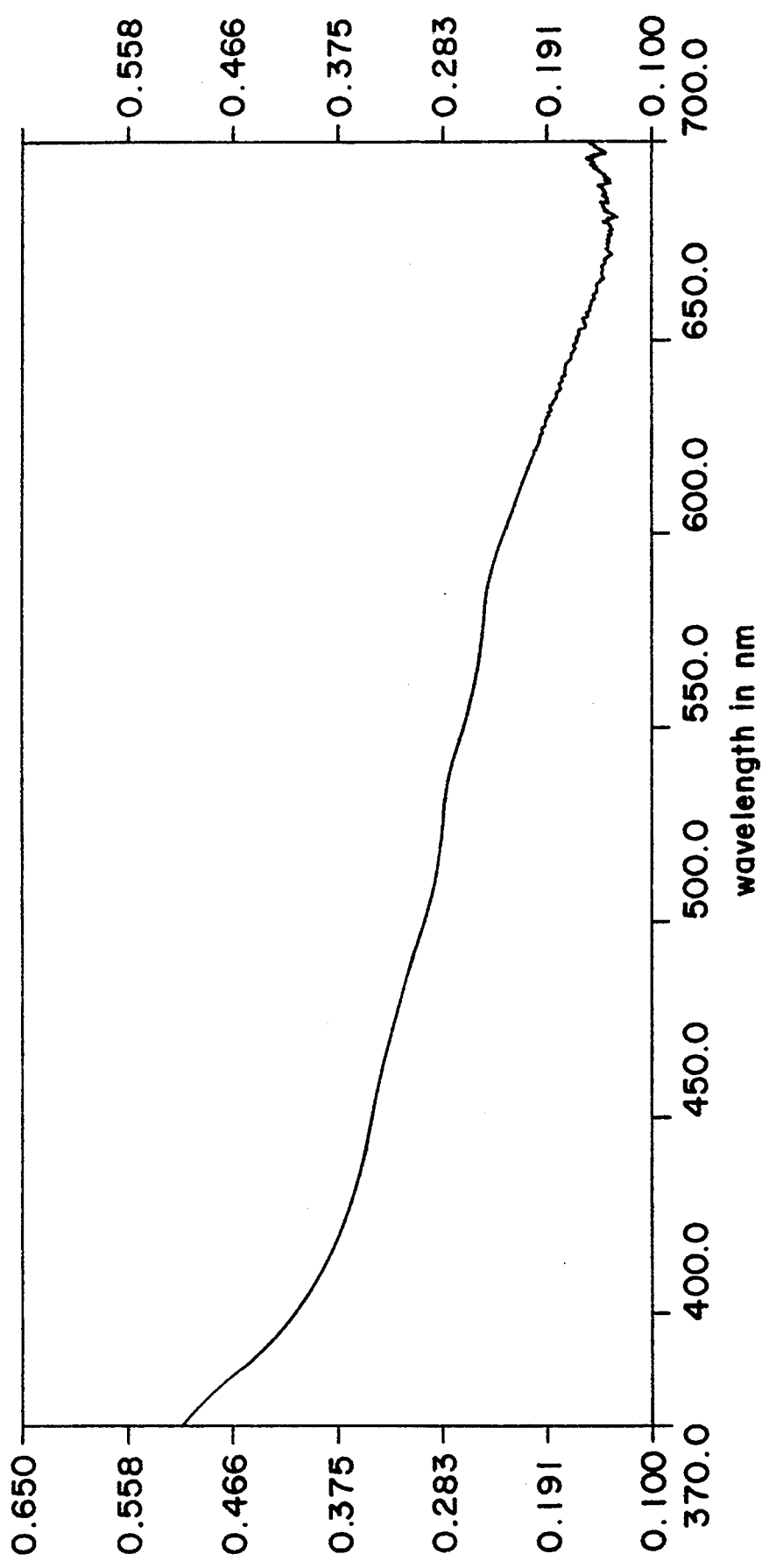

The $CuSO_4$-stained chromatogram corresponding to the lipid profile of 15 different AF samples is shown in FIG. 1. FIG. 2 represents the HPTLC profile obtained following scanning of lane o from FIG. 1. The ultraviolet and visible spectra of the $CuSO_4$-lipid chromogen following the charring reaction is shown in FIG. 3. The ultraviolet (FIG. 3A) and visible (FIG. 3B) spectra of the $CuSO_4$-lipid chromogen were acquired in the ranges between 200 and 370 nm and 370 and 700 nm, respectively, in the reflectance mode, using a Shimadzu CS-9000U spectrodensitometer for scanning.

Figure 4:
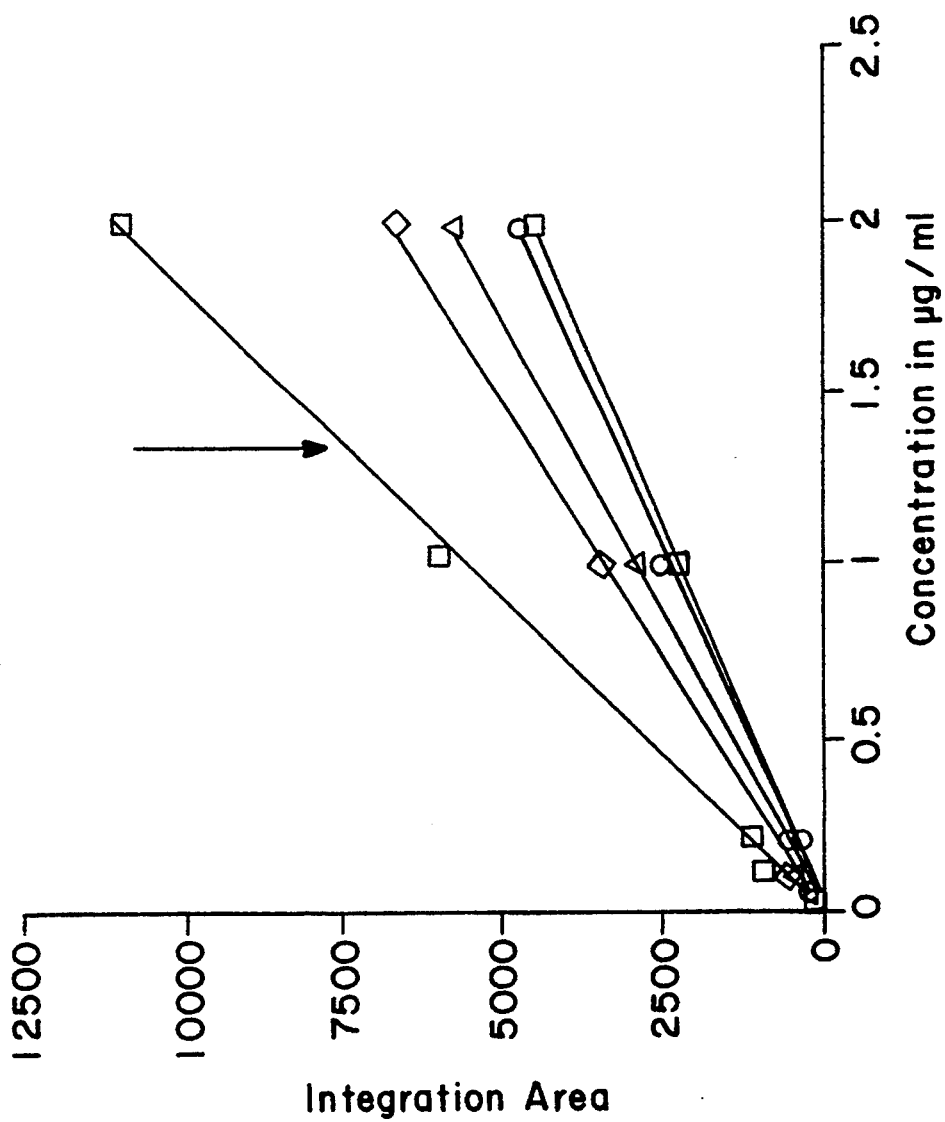
FIG. 4 is a graph illustrating the individual quantitative determinations of cholesteryl palmitate, phosphatidyl glycerol, phosphatidyl inositol, phosphatidyl choline and sphingomyelin obtained by high performance thin layer chromatography.

Finally, FIG. 4 illustrates the individual quantitative determinations of cholesteryl palmitate, phosphotidyl glycerol, phosphotidyl inositol, phosphotidyl choline and sphingomyelin obtained by high performance thin layer chromatography. To obtain the differential spectrum, the spectrum of a blank area of the plate we sfirst obtained and then subtracted by the computer of the spectrodensitometer from that obtained for the $CuSO_4$-lipid chromogen. Maximal absorbance was observed at 310 mm. As shown in Table E 1, scanning of the $CuSO_4$-lipid chromogen in the reflectance mode at 400 nm resulted in a signal ratio of 1.4 as compared to scanning in the transmittance mode at the same wavelength (the differential absorption, $\Delta A$, is maximal at 400 nm; $\Delta A = A_s - A_r$, $A_s$ and $A_r$ being the solute and layer absorption, respectively). Scanning in the transmittance mode at 310 nm is forbidden because of absorption of that wavelength by the glass of the plate. Scanning in the reflectance mode at 310 nm resulted in a signal ratio of 1.8 as compared to scanning in the reflectance mode at 400 nm. Therefore, scanning in the reflectance mode at 310 nm was selected for analysis of the $CuSO_4$-stained lipids.

TABLE E1

| Scanning Of the $CuSO_4$-Lipid Chromogen In The Transmittance And Reflectance Modes | | | |
|---|---|---|---|
| | Detector response | | |
| Scanning mode | 31 nm | 400 nm | 420 nm |
| Reflectance | 1.0 ± 0.05 | 0.71 ± 0.03 | 0.65 ± 0.03 |
| Transmittance | N.D. | 0.55 ± 0.02 | 0.45 ± 0.02 |

Values correspond to the detector response obtained following scanning of the $CuSO_4$-lipid chromogen at concentrations that ranged from 0.02 to 2μg and represent the mean (±S.D.) of five experiments; N.D=not determined.

Sample preparation time for the processing of 50 different AF samples, including sample transfer, C-M partition, and solvent evaporation, was 45 min. Sample application time, including sample delivery and rinsing cycles for all 50 samples, was 25 min. The combined predevelopment and development time was 35 min. All 25 lanes were scanned in the automatic mode at 1 cm s$^{-1}$ with an interlane scanning speed of 10 cm s$^{-1}$ and data accumulation time of 20 s per chromatogram. Total estimated time for scanning and data accumulation was 13 min.

Conclusions

The mode of analysis presented in this experimental series differs from other TLC methods in that (1) it only required 0.1-ml aliquots of amniotic fluid, (2) it uses 4.5 μm particle size high-performance layers that provide higher resolution only comparable to that obtained with HPLC columns, (3) sample application is automated, resulting in higher speed of analysis and precision, (4) all lipid classes, including phosphatidylglycerol and cardiolipin, often referred to as pseudophosphatidylglycerol, are separated in one dimension, therefore allowing multisample analysis, (5) the lipids are visualized with a highly sensitive lipid reagent that allows detection of picomole amounts of all lipids, (6) it provides quantitative data for lipids known to be associated with the fetal lung surfactant, and (7) a complete profile of AF lipids can be obtained in about 2 h for up to 50 samples.

The recoveries for the various lipids added to the AF following one single extraction ranged between 82 and 95%. The intra- and inter-assay variation, as measured by the relative standard deviation, were 4 and 8%, respectively. The lower limit of detection was 20 ng/ml with linear detector response extended to 2 µg/ml. This method constitutes a quantitative, sensitive, selective, reproducible, and high-capacity system for the analysis of the various lipids present in AF.

Experimental Series II: Assessment of

Fetal Lung Maturity

Samples:

The preferred protocol methodology described above was applied to the analysis of 50 amniotic fluids obtained either by transabdominal amniocentesis (n=40) or to fluids taken directly from the vaginal pool following premature rupture of membranes (n=10). Twenty three of these fluids were obtained from pregnant women whose babies developed RDS subsequently. The gestational ages of the patients (babies) included in the study ranged between 28 and 35 weeks. The levels of DPG in the fluids were compared with the clinical outcome (presence or absence of RDS in the child).

Results And Evaluation Procedure

Upon completion of the study, the following arbitrary DPG cut-off values were established in order to predict FLM. For all patients except diabetics (see below) the corresponding values were as follows: values <8 µg DPPC/mL was considered immature; values between 8 and 10 µg/mL were considered borderline; and values >10 µg/mL was considered mature. For diabetic patients, the corresponding values were as follows: <14 µg DPPC/mL the amniotic fluid sample was considered immature; values between 14 and 16 µg/mL were considered borderline; and values >16 µg/mL were considered mature.

The essential differences mature, immature, and borderline test results are demonstrated by FIGS. 5-10 respectively.

Figure 5:
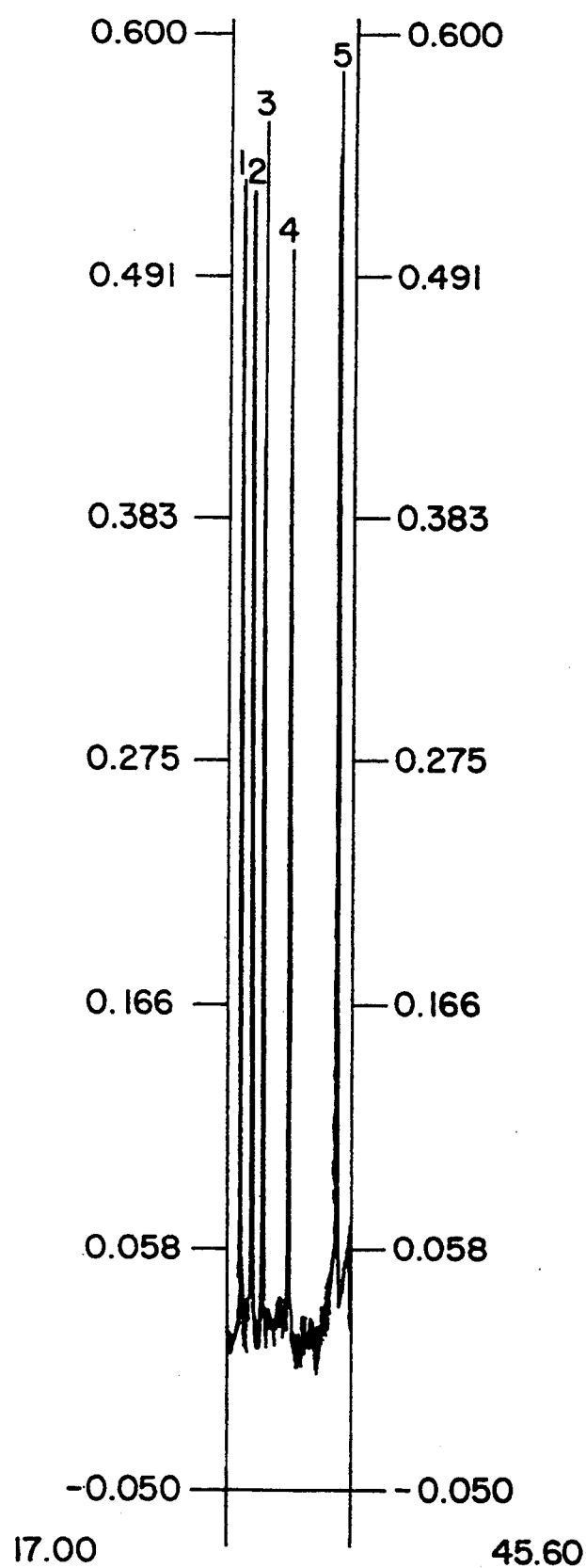
FIG. 5 is an illustration of a chromatogram showing the separation of the following diacylglycerol standards: 1:1,2-distearoyl glycerol; 2:1,2-dipalmitoyl glycerol; 3:1-palmitoyl, 2-myristoyl glycerol; 4:1-palmitoyl, 2-oleoyl glycerol; and 5:1,2-dioleoyl glycerol. Each peak corresponds to 0.4 µg of the corresponding diacylglycerol.
Figure 6:
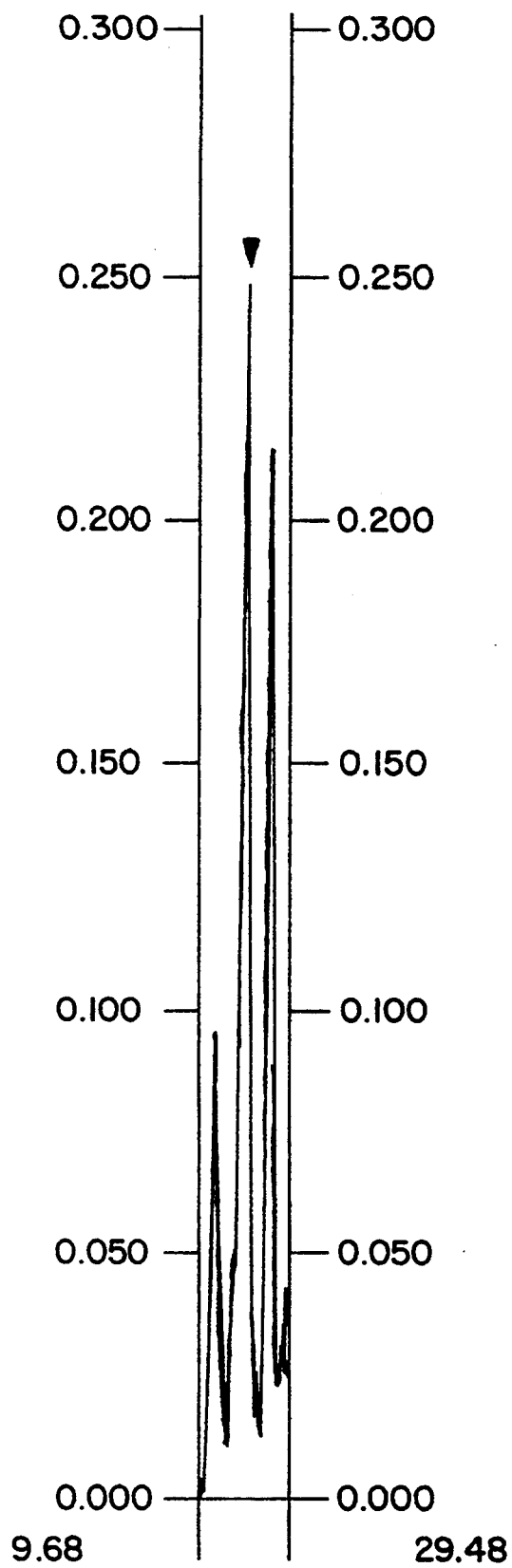
FIG. 6 is an illustration of a chromatogram from an amniotic fluid corresponding to a mature lung surfactant (DPG of 19 µg/mL).
Figure 7:
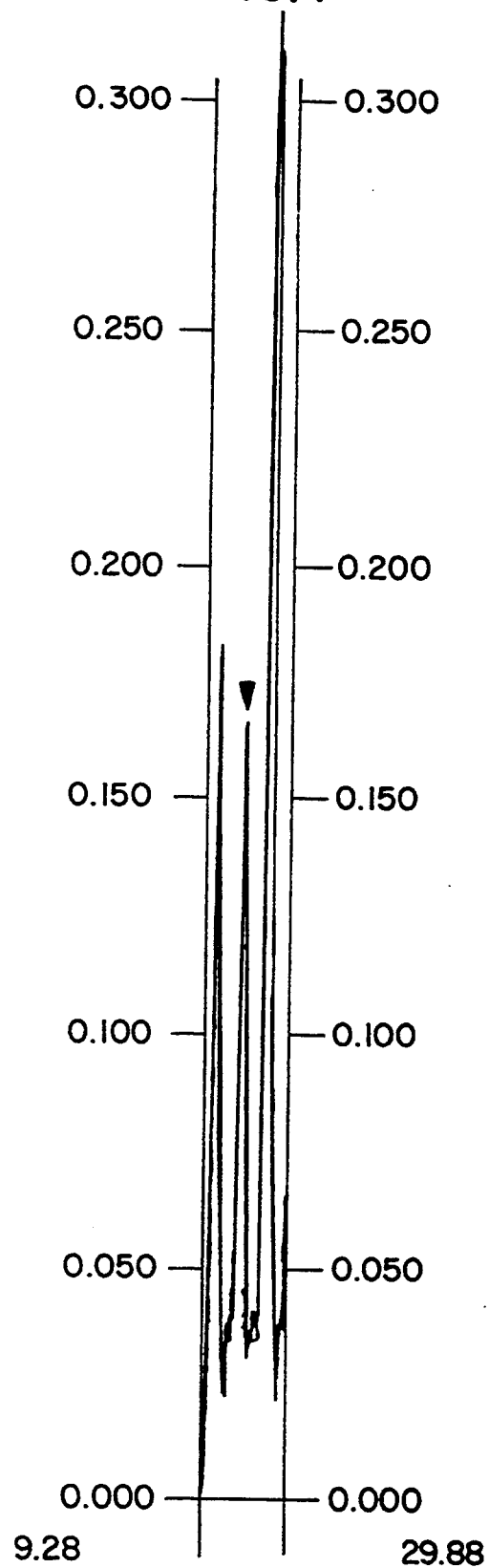
FIG. 7 is an illustration of a chromatogram from an amniotic fluid corresponding to a borderline lung surfactant (DPG of 8 µmL).
Figure 8:
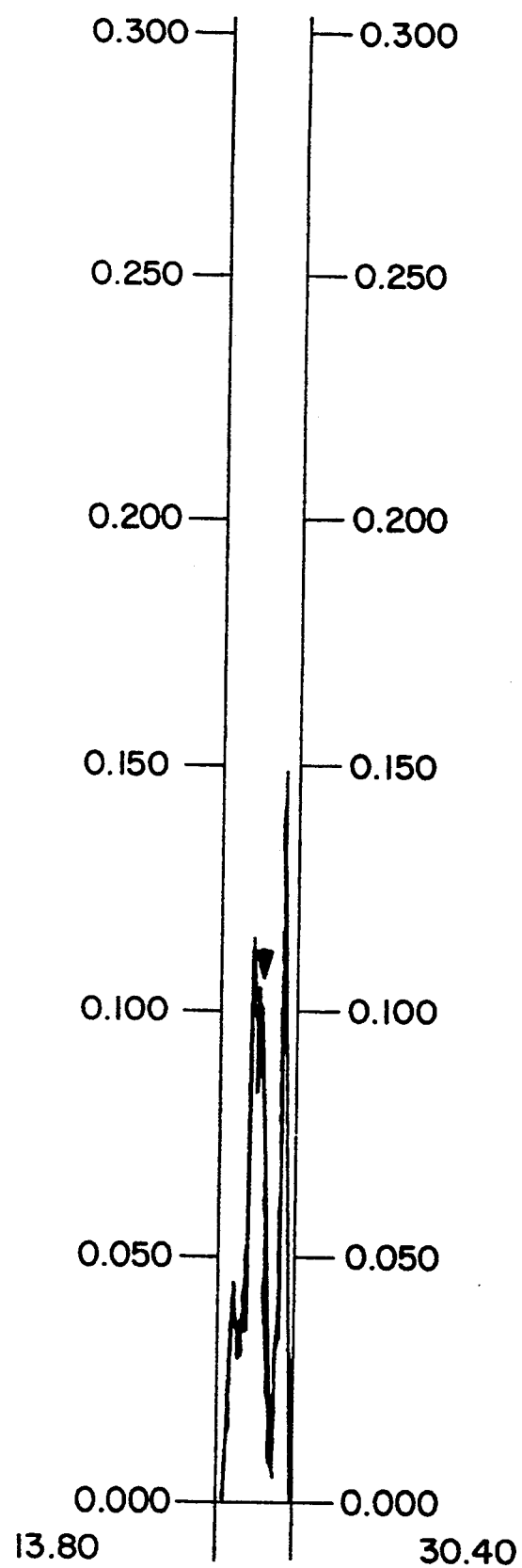
FIG. 8 is an illustration of a chromatogram from an amniotic fluid corresponding to an immature lung surfactant (DPG of 5.5 µg/mL); the infant was delivered within 72 hours of the test and developed RDS.
Figure 9:
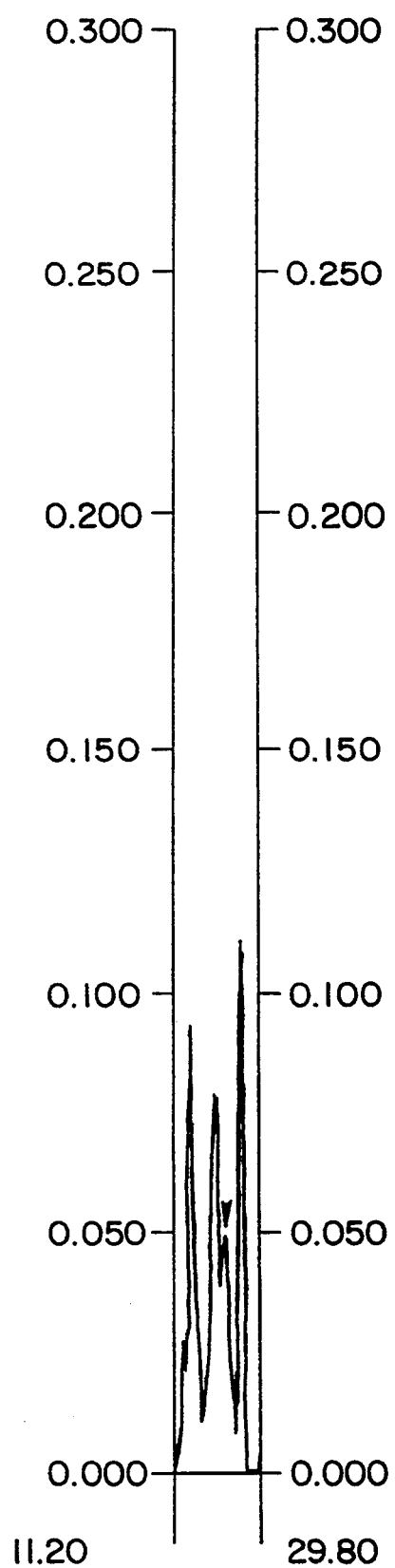
FIG. 9 is an illustration of a chromatogram from an amniotic fluid corresponding to a severely immature lung surfactant (DPG of 1.7 µg/mL); the infant was delivered within 72 hours of the test and developed RDS.
Figure 10:
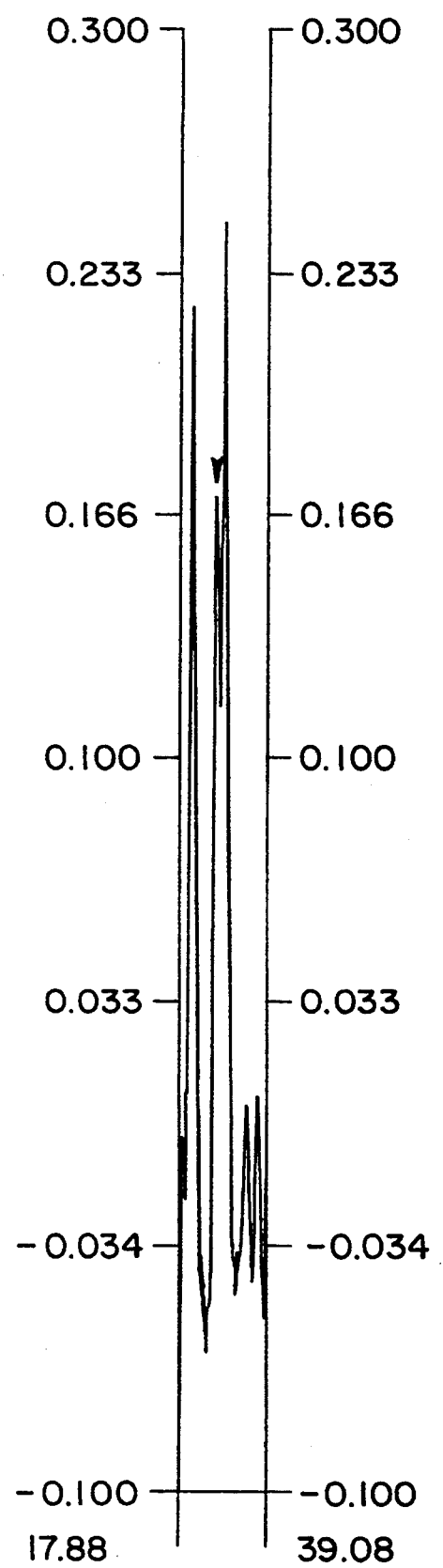
FIG. 10 is an illustration of a chromatogram from a blood-contaminated amniotic fluid corresponding to a mature lung surfactant (DPG of 13 µg/mL).

FIG. 5 represents a chromatogram of a mixture of diacylglycerol standards. 1 :dipalmitoyl glycerol; 2:dilauroyl glycerol; 3:dimyristoyl glycerol; 4:1-palmitoyl, 2-oleoyl glycerol; 5:dioleoyl glycerol. Each peak corresponds to 0.4 µg of the corresponding diacylglycerol. FIG. 6 represents a chromatogram of a mature amniotic fluid. The peak corresponding to DPG is indicated by the arrow. The actual concentration of DPG was calculated by interpolation of the area of integration corresponding to DPG from the sample with that obtained for the DPG internal standard. This value was 19 µg DPG/mL. FIG. 7 represents a chromatogram of a borderline amniotic fluid. The corresponding value was 8 µg DPG/mL. FIG. 8 represents a chromatogram of an immature amniotic fluid. The baby was delivered within 72 h of the test and developed RDS. The corresponding value was 5.5 µg DPG/mL. FIG. 9 represents a chromatogram of another immature amniotic fluid. The baby was delivered within 72 h of the test and developed severe RDS. Incubation of the baby was required. The corresponding value was 1.7µg DPG/mL and FIG. 10 represents a chromatogram of a mature blood contaminated amniotic fluid. The corresponding DPG value was 13 µg/mL.

Test Effectiveness

When these cut-off values were used to predict FLM in a large series of patients (n=150), the DPG test provided a sensitivity (ability to predict the presence of RDS) of 100% and a specificity (ability to predict the FLM) of at least 95%. Therefore, the DPG test provides a high specificity and high sensitivity means for the assessment of FLM.

In another study, the amniotic fluid samples were tested by both the DPG test described herein and the commercially available Abbott test. It was found that although the sensitivity of the Abbott test was between 95 and 100%, the specificity of the Abbott test was only 55%. In addition, since it is estimated that of all amniotic fluid samples sent for FLM analysis 15% are contaminated with either blood, creatinine, or meconium; and since the Abbott test is not suitable for the analysis of contaminated samples, this results in a net in an overall rate of falsely negative results of 60% (40% specificity).

The present invention shall not be limited in scope nor restricted in form except by the claims appended hereto.

What we claim is:

1. A method for assessing lung maturity of a fetus in a pregnant woman prior to labor, said method comprising tile steps of:

providing a sample of an amniotic fluid surrounding a fetus in a pregnant woman, said amniotic sample containing an aliquot of lung surfactant phosphoglycerides then present within the lungs of the fetus, wherein at least one of the phosphoglycerides is dipalmitoyl phosphatidyl choline (DPPC);

combining said amniotic fluid sample with at least one phospholipase as an enzyme reaction mixture for enzymatic cleavage of polar head moieties, of such lurig surfactant phosphoglycerides as are present in said sample and to release a plurality of diacylglycerols as enzyme reaction products, wherein at least one of said released diacylglycerols is dipalmatoyl glycerol (DPG);

adding at least one organic solvent to said enzyme reaction mixture for organic solvent extraction and fluid phase separation of said released plurality of diacylglycerols from the remainder of said enzyme reaction mixture, said extracted plurality of diacylglycerols residing within an isolatable organic solvent layer;

isolating and drying said organic solvent layer to yield an organic residue; and determining the quantity of DPG, in said organic residue using high performance thin layer chromatography detection means, wherein for a normal pregnant women, a value of less than 8 µg DPG/mL amniotic fluid is indicative of an immature fetal lung, a value of between 8 to 10 µg DPG/mL amniotic fluid is indicative of borderline maturity, and a value of greater than 10 μg DPG/mL amniotic fluid is indicative of a mature fetal lung; and for a diabetic pregnant women, a value of less than 14 μg DPG/mL amniotic fluid is indicative of an immature fetal lung, a value of between 14 to 16 μg DPG/mL amniotic fluid is indicative of borderline maturity, and a value of greater than 16 μg DPG/mL amniotic fluid is indicative of a mature fetal lung.

2. The assessment method as recited in claim 1 wherein said amniotic fluid sample comprises at least one contaminant selected from the group consisting of blood, meconium, creatinine, spermatozoa, vaginal secretions, and vaginal mucosal cells.

3. The assessment method as recited in claim 1 wherein said phospholipase for cleaving said lung surfactant phosphoglycerides is a phospholipase selected from the group consisting of phospholipase C, phospholipase D, phospholipase $A_1$, and phospholipase $A_2$.

4. The assessment method as recited in claim 1 wherein said organic solvent for extraction and separation of released diacylglycerols is a mixture of at least two compounds selected from the group consisting of hexane, toluene, diethyl ether, chloroform, acetone, ethanol and methanol.

5. A method for assessing lung maturity of a fetus in a pregnant woman prior to labor, said method comprising the steps of:

providing a sample of an amniotic fluid surrounding a fetus in a pregnant woman, said amniotic sample containing an aliquot of lung surfactant phosphoglycerides then present within the lungs of the fetus wherein at least one of the phosphoglycerides is dipalmitoyl phosphatidyl choline;

combining said amniotic fluid sample with at least one phospholipase as an enzyme reaction mixture for enzymatic cleavage of polar head moieties of such lung surfactant phosphoglycerides as are present in said sample and to release a plurality of diacylglycerols as enzyme reaction products, wherein at least one of said released diacylglycerols is dipalmatoyl glycerol (DPG);

adding at least one organic solvent to said enzyme reaction mixture for organic solvent extraction and fluid phase separation of said released plurality of diacylglycerols from the remainder of said enzyme reaction mixture, said extracted plurality of diacylglycerols residing within an isolatable organic solvent layer; isolating and drying said organic solvent layer to yield an organic residue;

reconstituting the organic residue with an organic solvent mobile phase and depositing the organic residue on an $AgNO_3$ coated silica plate solid phase for separating the DPG from other diacylglycerols;

staining the silica plate with $CuSO_4$; and detecting and determining the quantity of DPG with scanning spectrodensitometry, wherein for a normal pregnant women, a value of less than about 8 μg DPG/mL amniotic fluid is indicative of immature fetal lungs, a value of between 8 to 10 μg DPG/mL amniotic fluid is indicative of borderline maturity, and a value of greater than 10 μg DPG/mL amniotic fluid is indicative of mature fetal lung; and for a diabetic pregnant woman, a value of less than 14 μg DPG/mL amniotic fluid is indicative of immature fetal lungs, a value of between 14 to 16 μg DPG/mL amniotic fluid is indicative of borderline maturity, and a value of greater than 16 μg DPG/mL amniotic fluid is indicative of a mature fetal lung.

6. The assessment method as recited in claim 5 wherein said phospholipase for cleaving said lung surfactant is a phospholiphse selected from the group consisting of phospholipase C, phospholipase D, phospholipase $A_1$ and phospholipase $A_2$.

7. The assessment method as recited in claim 5, wherein said organic solvent for extraction and separation of released diacylglycerols is a mixture of at least two compounds selected from the group consisting of hexane, toluene, diethyl ether, chloroform, acetone, ethanol and methanol.

* * * * *